United States Patent [19]

Tobkes et al.

[11] 4,196,199

[45] Apr. 1, 1980

[54] ANTIBIOTIC BM123 SYNTAN COMPLEXES

[75] Inventors: Martin Tobkes, Spring Valley; Murray Dann, Pearl River, both of N.Y.

[73] Assignee: American Cyanamid Company, Stamford, Conn.

[21] Appl. No.: 874,307

[22] Filed: Feb. 2, 1978

[51] Int. Cl.$^2$ ............................ A61K 31/70; A61K 31/71
[52] U.S. Cl. .............................. 424/180; 424/181; 536/17 R
[58] Field of Search ................... 536/17; 424/181, 180

[56] References Cited

U.S. PATENT DOCUMENTS 4,007,167  2/1977  Mautin et al. ........................ 536/17

Primary Examiner—Jerome D. Goldberg
Attorney, Agent, or Firm—Edward A. Conroy, Jr.

[57] ABSTRACT

This disclosure describes reversible complexes of antibiotic trans-BM123γ with a synthetic tanning agent and a process for preparing same. The complexes are useful as animal feed supplements which significantly enhance the growth rate of animals and poultry.

7 Claims, No Drawings

ANTIBIOTIC BM123 SYNTAN COMPLEXES

BRIEF SUMMARY OF THE INVENTION

This invention relates to a method of recovering antibiotic trans-BM123γ from fermentation whole harvest mashes containing it. More particularly, the process involves adding a synthetic tanning agent either to the whole harvest mash or to the filtered fermentation liquor, and recovering the so precipitated antibiotic-syntan reversible complex by any convenient means. The invention also relates to the use of the so prepared complexes in animal feed supplement compositions for enhancing the growth rate of animals such as poultry, swine, early weaned pigs, and ruminants such as cattle, sheep and goats.

DETAILED DESCRIPTION OF THE INVENTION

Antibiotic trans-BM123γ is formed by fermentative biosynthesis during the cultivation under controlled conditions of new strains of an undetermined species of Nocardia NRRL 5646, NRRL 8050, NRRL 11230 and mutants thereof. The preparation and properties of antibiotics trans-BM123γ$_1$, trans-BM123γ$_2$, and trans-BM123γ are set forth in U.S. Pat. No. 4,007,167 which is hereby incorporated by reference. Hereinafter, trans-BM123γ refers to a mixture in any proportions of trans-BM123γ$_1$ and trans-BM123γ$_2$. The problem of recovering the antibiotic economically has been a serious one. In the patent referred to above, adsorption on carbon followed by elution and column chromatography are employed. Such a process is not excessively expensive where pure antibiotic is required for medical usage. However, when the antibiotic is to be used in animal feed supplement compositions the factor of cost is a very serious matter and there is, therefore, a need for an inexpensive process of recovering the antibiotic for this purpose.

The present invention deals with a process and in a more specific aspect also with a product. The process involves the precipitation of the antibiotic either from the whole harvest mash or from the filtered fermentation broth by the addition of a synthetic tanning agent. The synthetic tanning agent operable in the novel process of the present invention is a sulfited phenol formaldehyde condensate which may be represented by the following general formula:

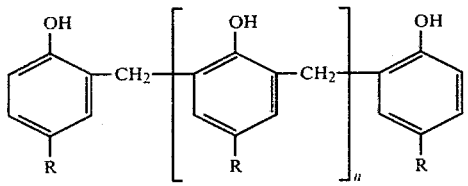

wherein R is hydrogen or a methylene sulfonic acid group (—CH$_2$SO$_3$H) and n is 0,1,2,3, or 4 with the proviso that about half of the R groups present are methylene sulfonic acid groups. This synthetic tanning agent is not a pure chemical compound but of necessity is obtained as a mixture having an estimated molecular weight of 420–530. It is readily prepared by first condensing phenol and formaldehyde in aqueous media followed by reaction of the intermediate condensate with formaldehyde, various sulfites, and buffer acids thus forming ω-sulfonic acid groups (—CH$_2$SO$_3$H) in the molecule. The product is an amorphous water soluble material that may be obtained either in concentrated water solution or in powder form, and ranges from colorless to dark brown. In order to avoid cumbersome language, this synthetic tanning agent will be referred to by its generic name in the art as "syntan", and this term will be used extensively in the specification and appended claims. A sulfited phenol formaldehyde syntan of the above general type is sold by A. J. & J. O. Pilar Inc. of Newark, N.J. under the trademarks Tru-Tan ® RT Regular and Trutan ® RT New.

The novel process of the present invention provides almost complete removal of the antibiotic activity from the fermentation mash or broth. Furthermore, the antibiotic-syntan complex so obtained can be used without separation of the constituents in animal feed supplement compositions, which is an important economic advantage. Therefore, in one of the aspects of the present invention the complex of antibiotic trans-BM123γ and the above-described syntan is included as a new product.

The product of the antibiotic and the syntan has been referred to as a reversible antibiotic-syntan complex. Its exact chemical nature has not been determined, but covalent bonding is not involved and the product is not a physical mixture. This complex, derived from the interaction of the antibiotic and the syntan, is not necessarily combined in any limiting stoichiometry. The chemical bonds are reversible since antibiotic trans-BM123γ may be recovered from the complex by adsorption on a cross-linked carboxymethyldextran gel column followed by elution with aqueous acid. While it is not intended to limit the present invention to theories of chemical constitution and the like, it seems probable that the complex of the present invention is sufficiently reversible so that under conditions of use in animal feed supplement compositions the antibiotic is set free upon ingestion.

As starting material for the novel process of the present invention there may be employed the whole harvest mash obtained after completion of a fermentation with Nocardia sp. NRRL 5646, NRRL 8050, NRRL 11230 or mutants thereof. Preferably, there is employed the fermentation liquor or broth which has been clarified by removing the mycelia and other insolubles by filtration. Diatomaceous earth or any other conventional filtration aid may be used to assist in the filtration. In either case, the pH of the whole mash or the filtered broth may be first adjusted to between 1.8 and 5.0 with dilute aqueous acid. Suitable acids for this purpose may be, for example, dilute hydrochloric acid, dilute sulfuric acid, dilute trifluoroacetic acid, etc., although even glacial acetic acid may be used. Then an aqueous solution of the syntan is added slowly, with stirring, at ambient temperatures. The pH may then be adjusted at this point to 1.8–5.0 by acidifying as above or basifying with a suitable base such as aqueous ammonia or soda ash. The antibiotic and the syntan form a complex which is water insoluble and thus precipitates. The precipitated syntan complex or, in the case of the whole mash, the precipitated syntan complex together with the fermentation mash solids, is then removed by filtration or centrifugation and dried. The products so obtained may be dried by (1) slurrying the wet solids in polar, water miscible non-solvents such as acetone followed by filtration, rinsing and air-drying; or by (2) reslurrying the wet solids in water and freeze drying or spray drying.

When the products of the present invention are thus carefully dried under temperature conditions which do not degrade antibiotic trans-BM123γ, they are usually white to tan powders in the case of the syntan complex. In the case of the syntan complex associated with dried harvest mash solids, they are usually gray to brown powders or solids. In the dry form, these products are extremely stable, keeping without significant loss of antibiotic activity for considerable periods of time. This long storage life is, of course, an important practical advantage.

It is an advantage of the present invention that the amount of syntan added to precipitate the complex is not critical and no exact stoichiometric relations need be followed. In general, the amount of syntan used will be somewhat in excess of the minimum required to form the complex with the antibiotic. Excess syntan will merely remain in solution upon filtration. The amount of syntan required is, however, directly proportional to the antibiotic concentration in the mash or liquor. The specific bioactivity of the precipitated complex also varies and it is in fact likely that the complex has varying relative amounts of antibiotic and, of course, is quite likely to be a mixture of complexes because the syntan used is not a pure single chemical compound.

The minimum amount of syntan required to form the complex with the antibiotic in any particular fermentation batch may be readily determined as follows. A sample (conveniently 50–100 ml.) of the fermentation whole harvest mash is taken and clarified by removing the mycelia and other insolubles by filtration, preferably with a filter aid. The filtrate is then acidified to a pH of 1.8–5.0 with dilute aqueous mineral acid such as dilute hydrochloric acid, dilute sulfuric acid, dilute phosphoric acid, or the like. This solution is then titrated with the particular aqueous solution of syntan which is to be used until no further precipitate or turbidity forms. The amount of syntan solution for the fermentation batch is then calculated from the titer of the sample taken, providing also for a slight excess.

This invention also relates to animal feed supplement compositions effective in accelerating the growth rate of animals and poultry. In recent years the use of antibiotics in animal feeds for improving growth characteristics and efficiency of feed utilization has become of considerable economic importance. In accordance with the present invention, the dried syntan complex or the dried harvest mash solids containing the syntan complex, either alone or in combination with suitable carriers, when added to an animal feed aid in increasing the growth rate. In addition, feed efficiency is improved. The present invention has the advantage that the growth rate of non-ruminants such as poultry and swine and especially weanling pigs is significantly increased, and that feed conversion rates are noticeably enhanced.

The feed supplement compositions of the present invention are administered in an amount sufficient to furnish approximately the following dosage levels in mg./head/day:

| | |
|---|---|
| Large ruminants | 350 |
| Small ruminants | 200 |
| Non-ruminants | 100 |
| Poultry | 2 |

The milligrams per pound of antibiotic trans-BM123γ present in any particular supplement composition of the present invention may be readily determined by bioassay as set forth in U.S. Pat. No. 4,007,167. The preferred method is an adaptation of the *Staphylococcus aureus* turbidimetric assay for tetracycline that is described in the manual "*Assay Methods of Antibiotics, a Laboratory Manual*" by D. C. Grove and W. A. Randall, Medical Encyclopedia Inc. (1955) pages 48–52, substituting *Klebsiella pneumoniae* as the test organism. From the potency data thus obtained, the pounds of feed supplement composition to be used per ton of feed may be readily calculated.

A wide variety of carriers may be used in the preparation of the feed supplement compositions of this invention containing the dried syntan complex or the dried harvest mash solids containing the syntan complex. Carriers suitable for use to make up the feed supplement compositions include the following: soybean meal, alfalfa meal, cotton seed oil meal, linseed oil meal, cornmeal, cane molasses, urea, bone meal, corncob meal, and the like. The carrier promotes a uniform distribution of the complex in the finished feed into which the supplement is blended. It thus performs an important function by ensuring proper distribution of the complex throughout the feed.

For a clearer understanding of the invention, specific examples of it are set forth below. These examples are merely illustrative, and are not to be understood as limiting the scope and underlying principles of the invention in any way.

EXAMPLE 1

Preparation of Antibiotic trans-BM123γ—Syntan Complex from Whole Harvest Mash

Thirty liters of Nocardia sp. NRRL 11230 fermentation mash containing 347 mcg. of trans-BM123γ antibiotic per ml. is used at harvest pH 5.7. A 750 ml. portion of TruTan ® RT New is added slowly to the mash with stirring. The mixture is stirred for one hour, 600 g. of diatomaceous earth is added and the mixture is filtered. The filter cake is dried in vacuo at 40° C. for 48 hours, giving 1.5 kg. of dried material containing the antibiotic trans-BM123γ—syntan complex.

Nocardia sp. NRRL 11230 has cultural, physiological, and morphological characteristics essentially the same as those of NRRL 5646 and NRRL 8050.

EXAMPLE 2

Preparation of Antibiotic trans-BM123γ—Syntan Complex from Harvest Mash Filtrate To 3 liters of stirred Nocardia sp. NRRL 11230 fermentation mash filtrate, assaying 475 mcg. of antibiotic trans-BM123γ per ml. is added 52.5 ml. of TruTan ® RT New. The pH of the resultant slurry is adjusted to 4.75 with 6 N hydrochloric acid, stirred for 5 minutes and allowed to settle for 45 minutes. The solids are recovered by filtration, washed with a small amount of water and dried in vacuo, without heat, giving 35.18 g. of product.

EXAMPLE 3

Growth Promoting Effect of Antibiotic trans-BM123γ—Syntan Complex on Poultry

One day old Hubbard X Hubbard crossbred chicks were used. These chicks are randomly allotted to pens of ten chicks (5 male and 5 female) each. Four experiments are started at one week intervals. In each experiment, four pens of chicks are used for unmedicated controls and two pens of chicks are used at each level of drug. Thus, a total of 16 pens (160 chicks) are used as controls and a total of 8 pens (80 chicks) are used at each level of drug. The duration of each experiment is 13 days.

The controls are offered an unmedicated diet of broiler ration (composition follows) and water ad libitum. The medicated chicks are offered the same diet containing antibiotic trans-BM123γ—TruTan® RT New complex at levels of 1, 2, 5, 10, 20 and 30 parts per million and water ad libitum. The weight of the chicks is determined at the beginning and on completion of the experiments. Weight gain and the amount of feed consumed are also determined. The data are averaged and summarized in Table I below, together with the percent improvement in weight gains and feed/gain ratios.

| Broiler ration formula: Component | Percent by weight |
|---|---|
| Ground yellow corn | 53.45 |
| Soybean oil meal (49%) | 28.00 |
| Menhaden fish meal (60%) | 5.00 |
| Corn gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |

| *Trace mineral mixture Component | | One lb./ton furnishes |
|---|---|---|
| Manganese | 12.50% | 62.5 ppm |
| Iron | 6.00% | 30.0 ppm |
| Zinc | 5.00 | 25.0 ppm |
| Copper | 0.65% | 3.25 ppm |
| Iodine | 0.35% | 1.75 ppm |
| Cobalt | 0.25% | 1.25 ppm |
| Calcium (min. 15.30%, max. 18.35%) | | |

| **Vitamin premix for one ton Component | Weight in grams |
|---|---|
| DL. Methionine | 453.6 |
| Butylated hydroxy toluene | 113.6 |
| Vitamin A (30,000 mcg./g.) | 100.0 |
| Vitamin D₃ (200,000 mcg./g.) | 5.0 |
| Vitamin E (20,000 mcg./lb.) | 45.4 |
| Riboflavin | 4.0 |
| Niacinamide | 25.0 |
| Calcium pantothenate | 8.0 |
| Vitamin K (menadione) | 1.0 |
| Folic acid (10%) | 13.0 |
| Choline chloride (50%) | 908.0 |
| Vitamin B₁₂ (20 mg./lb.) | 227.0 |
| Corn oil | 50.0 |
| Fine ground corn | 2,582.4 |

We claim:
1. A process of recovering an antibiotic trans-BM123γ—syntan complex from a fermentation whole harvest mash containing antibiotic trans-BM123γ which comprises the steps of:
   a. producing a fermentation liquor by filtering the whole harvest mash;
   b. adding to the fermentation liquor a syntan complexing agent comprising a mixture of compounds of the formula:

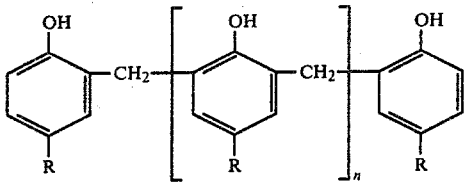

wherein R is hydrogen or methylene sulfonic acid and n is 0, 1, 2, 3, or 4 with the proviso that about half of the R's present are methylene sulfonic acid, until a sufficient amount of the antibiotic trans-BM123γ—syntan complex is imparted to said medium;
   c. adjusting the medium to a pH of from 1.8 to 5.0 with a pharmacologically acceptable acid or base;
   d. removing the precipitated antibiotic trans-BM123γ—syntan complex; and
   e. drying the antibiotic trans-BM123γ—syntan complex.

2. A dry complex of a syntan with antibiotic trans-BM123γ prepared as defined in the process of claim 1.

3. A process for the production of a dried fermentation harvest mash solids animal feed supplement containing an effective amount of antibiotic trans-BM123γ—syntan complex which comprises the steps of:
   a. adding to the fermentation whole harvest mash a syntan complexing agent comprising a mixture of compounds of the formula:

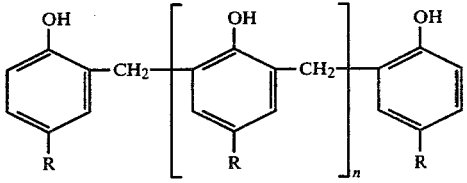

wherein R is hydrogen or methylene sulfonic acid and n is 0, 1, 2, 3, or 4 with the proviso that about half of the R's present are methylene sulfonic acid, until a suffi-

TABLE I

| Treatment | Drug Level In Feed (ppm) | Av. Weight Per Chick In Grams | | Av. Weight Gain Per Chick In Grams | Feed Consumed Per Chick In Grams (Average) | Feed/Gain Ratio | % Improvement In | |
|---|---|---|---|---|---|---|---|---|
| | | Start | End | | | | Gain | Feed/Gain Ratio |
| Control | 0 | 44.0 | 239.3 | 195.4 | 292.1 | 1.495 | | |
| Antibiotic | 1 | 44.1 | 245.2 | 201.2 | 294.0 | 1.461 | 3.0 | 2.3 |
| trans-BM123γ- | 2 | 44.0 | 244.4 | 200.4 | 296.2 | 1.478 | 2.6 | 1.1 |
| TruTan® RT | 5 | 44.0 | 249.4 | 205.4 | 292.9 | 1.426 | 5.1 | 4.6 |
| New Complex | 10 | 44.0 | 251.8 | 207.8 | 299.6 | 1.442 | 6.3 | 3.5 |
| | 20 | 44.0 | 251.8 | 207.8 | 302.1 | 1.454 | 6.3 | 2.7 |
| | 30 | 44.0 | 248.1 | 204.1 | 294.9 | 1.445 | 4.5 | 3.3 | cient amount of the antibiotic trans-BM123γ—syntan complex is imparted to said medium;
   b. adjusting the medium to a pH of from 1.8 to 5.0 with a pharmacologically acceptable acid;
   c. removing the harvest mash solids together with the precipitated antibiotic trans-BM123γ—syntan complex; and
   d. drying the mixture of mash solids and antibiotic trans-BM123γ—syntan complex.

4. An animal feed supplement of a dry mixture of fermentation harvest mash solids and an effective amount of antibiotic trans-BM123γ—syntan complex prepared in accordance with the process of claim 3.

5. An animal feed composition for improving feed efficiency and enhancing the growth rate of animals and poultry comprising a nutritionally balanced animal feed containing from about 0.0001% to about 1.0% by weight of the feed of an antibiotic trans-BM123γ—syntan complex prepared as defined in the process of claim 1.

6. An animal feed composition for improving feed efficiency and enhancing the growth rate of animals and poultry comprising a nutritionally balanced animal feed containing from about 0.0001% to about 1.0% by weight of the feed of an animal feed supplement prepared as defined in the process of claim 3.

7. An animal feed premix for improving feed efficiency and enhancing the growth rate of animals and poultry comprising from about 70% to about 99% by weight of an edible carrier and from about 1% to about 30% by weight of an antibacterial ingredient selected from the group consisting of a dry complex as defined in claim 2, an animal feed supplement as defined in claim 4, and mixtures thereof in any proportion.

* * * * *